(12) United States Patent
Yu

(10) Patent No.: US 7,210,253 B2
(45) Date of Patent: May 1, 2007

(54) MASSAGE SHOES CAPABLE OF INCREASING CIRCULATION OF BLOOD

(76) Inventor: Tsung I Yu, No. 209, Sec. 3, County Boulevard, Pan Chiao City, Taipei (TW)

( * ) Notice: Subject to any disclaimer, the term of this patent is extended or adjusted under 35 U.S.C. 154(b) by 159 days.

(21) Appl. No.: 11/052,027

(22) Filed: Feb. 8, 2005

(65) Prior Publication Data

US 2006/0174522 A1     Aug. 10, 2006

(51) Int. Cl.
*A61F 5/14* (2006.01)
*A61H 1/00* (2006.01)

(52) U.S. Cl. ............................. 36/141; 601/46; 601/30
(58) Field of Classification Search .................. 36/141, 36/136; 601/30, 46
See application file for complete search history.

(56) References Cited

U.S. PATENT DOCUMENTS 4,802,463 A * 2/1989 Rojas ........................... 36/141
5,113,850 A * 5/1992 Larremore et al. ........... 601/46
5,592,759 A * 1/1997 Cox .............................. 36/141
5,836,899 A * 11/1998 Reilly .......................... 36/141
5,913,838 A * 6/1999 Reilly .......................... 36/141

* cited by examiner

*Primary Examiner*—Ted Kavanaugh
(74) *Attorney, Agent, or Firm*—Bacon & Thomas PLLC

(57) ABSTRACT

A massage shoe comprises a controller and a shoe body. The inner foot supporting surface of the shoe body is provided with a plurality of conducting sheets, which are respectively connected by conducting wires to a selected location on a vamp or in the heel of the shoe body, and then to the controller for providing a foot with a mid-or-low-frequency electromagnetic wave massage. The controller can be separated from the shoe body and controls the shoe body by a wired or a wireless means. The controller can be connected to other electric massage devices for supplying pulses. The heel of the shoe body is provided with a polarity switch for changing polarity of each of the conducting sheets, whereby the massage effect can be local to a foot or global across two feet, if a pair of shoe bodies is electrically connected.

16 Claims, 14 Drawing Sheets

MASSAGE SHOES CAPABLE OF INCREASING CIRCULATION OF BLOOD

BACKGROUND OF THE INVENTION (a) Field of the Invention

The present invention relates to massage shoes, more particularly to a type of massage shoes capable of applying a low-frequency electromagnetic wave massage to the sole of a foot or other foot portions enclosed in a shoe of this type.

(b) Description of the Prior Art

A pair of shoes of the prior art, such as slippers, sandals, sneakers, leather shoes, mountaineering boots and informal shoes, has a single effect of enclosing and protecting foots. The shoes cannot provide a function of enhancing blood circulation for the enclosed foots. The massage shoes of the prior art are usually provided with a plurality of granules or magnets, mounted on the shoe soles, for a massage effect through direct contact. However, the massage shoes of this type would cause discomfort to a user and therefore are not practical.

The current known prior arts about massage control are for example, U.S. Pat. No. 6,210,771B1, U.S. Pat. No. 6,021,353 which discloses the control with periodic massaging effect. Further U.S. Pat. No. 6,151,528 discloses a massage trousers with conductive sheets.

SUMMARY OF THE INVENTION

Accordingly, the primary objective of the present invention is to provide a pair of massage shoes comprises two shoe bodies and a controller. The shoe pad of each of the shoe bodies is provided with a plurality of conducting sheets. Each of the conducting sheets is electrically connected by a conducting wire; the conducting wires are converged toward a selected location on a vamp or in the heel of a shoe body. Thereby, the controller can transmit electric signals to the conducting sheets for providing a low-frequency electromagnetic wave massage.

The secondary objective of the present invention is to provide massage shoes wherein a polarity switch is installed for changing the electric polarity of each of the conducting sheets. Further, the electric connection between two shoe bodies can be varied so as to provide a low-frequency electromagnetic wave massage to a single foot or both feet.

The third objective of the present invention is to provide massage shoes wherein the controller is connected to the shoe bodies by either a wireless means or a wire.

It is a further objective of the present invention that the batteries for the controller can be a separate entity from the controller or contained within the controller.

It is a further objective of the present invention that the controller can also power other massage devices, such as a conducting gloves and a conducting massage stick, while it is powering the shoes. Thereby, a whole body massage can be provided.

It is a further objective of the present invention that the insoles of the shoes can be respectively provided with insulating shoe pads having a plurality of conducting patches corresponding to acupuncture points on the bottom side of a foot, whereby a low-frequency electromagnetic wave massage will be concentrated at those points.

The various objects and advantages of the present invention will be more readily understood from the following detailed description when read in conjunction with the appended drawings.

DETAILED DESCRIPTION OF THE PREFERRED EMBODIMENTS

Figure 1:
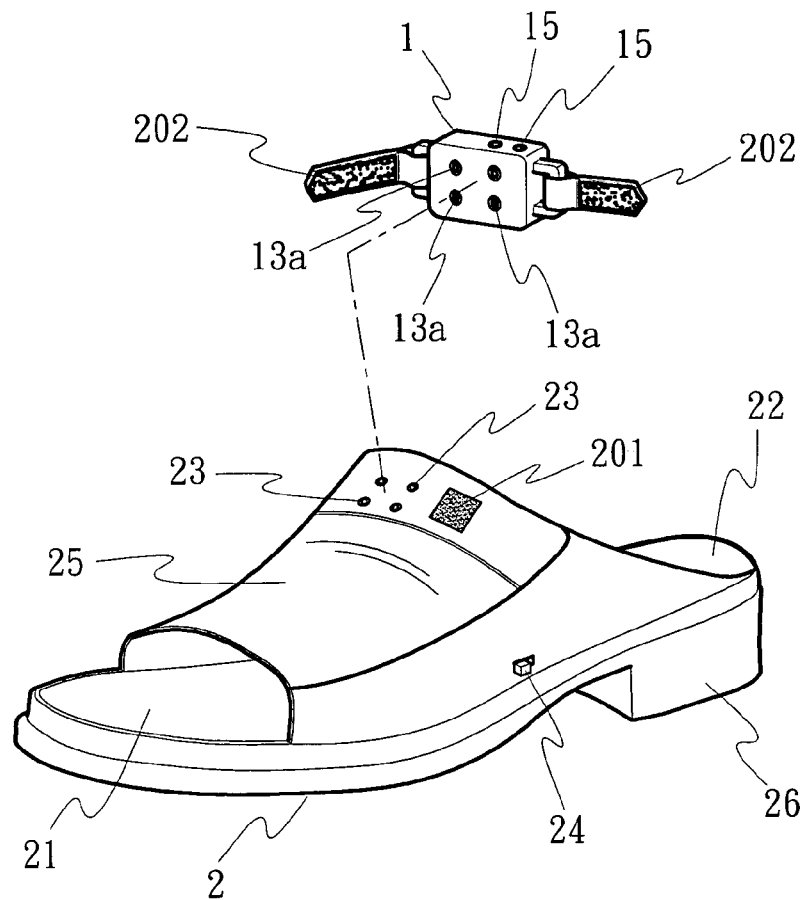
FIG. 1 is a perspective view showing a controller removed from a shoe body.
Figure 2:
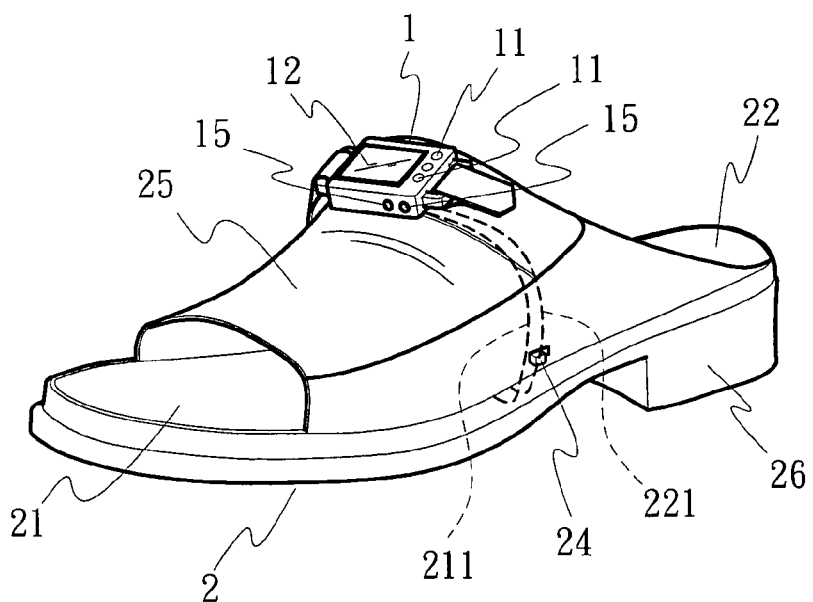
FIG. 2 is a perspective view showing the controller and the shoe body in FIG. 1 combined.

Referring to FIGS. 1 and 2, a massage shoe according to the present invention comprises a controller 1 and a shoe body 2. The inner foot supporting surface is provided with a plurality of conducting sheets 21, 22, which are respectively connected by conducting wires 211, 221 to a selected location in the shoe body 2. The selected location forms a plurality of conducting snap sockets 23 for connecting and securing the controller 1, whereby the controller 1 can transmit electric signals to the conducting sheets 21, 22 for providing a mid-or-low-frequency electromagnetic wave massage to the foot in contact with the conducting sheets 21, 22. Further, the shoe body 2 is provided with a polarity switch 24 for changing the electric polarities of the conducting sheets 21, 22, whereby the conducting sheets 21, 22 can be of one polarity or different polarities. Use two a pair of such shoe bodies 2 together, the polarity switch 24 can set each of the shoe bodies 2 is uniformly polarized, whereas two shoe bodies 2 are of different polarities. This will induce a global massage across two feet. On the other hand, the polarity switch 24 can also set the conducting sheets 21, 22 in each of the shoe bodies 2 at different polarities, whereby each foot will have independent local massage.

The controller 1 has a central integrated circuit (IC) for generating and transmitting electric pulses, whereby the inductors and capacitors therein will be charged. The pulses are then modified by programs to have a bandwidth in the range of 1 Hz to 150 Hz, achieving massage effect of variable strength. The controller 1 further includes a plurality of control keys 11 respectively for adjusting the magnitude of electric current, setting operating time and setting massage modes. The controller 1 further comprises an LCD display 12 to display the current operating mode to a user. The modified pulses are sent out through an output terminal having a plurality of conductive terminals 13a, which can be engaged with the conducting snap sockets 23 of the shoe body 2. The conductive terminals 13a of the controller 1 may have other adhesive straps 201, 201 for assisting securing the controller 1 onto the shoe body 2. The shoe body 2 has a polarity switch 24 for controlling the polarities of the conducting sheets 21, 22.

16. The pair of massage shoes of claim 12 wherein the controller has at least two sockets 15 for being connected to other peripheral conductive device (identical to those illustrated in FIGS. 11 and 12).

Figure 3:
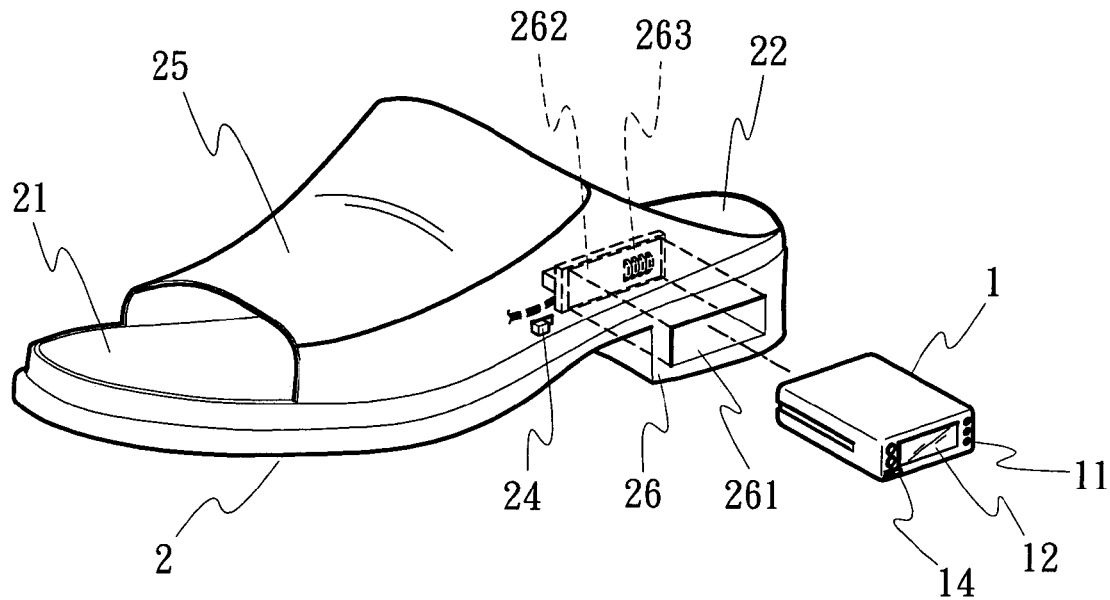
FIG. 3 shows another preferred embodiment of the present invention wherein a controller is removed from a shoe body.
Figure 4:
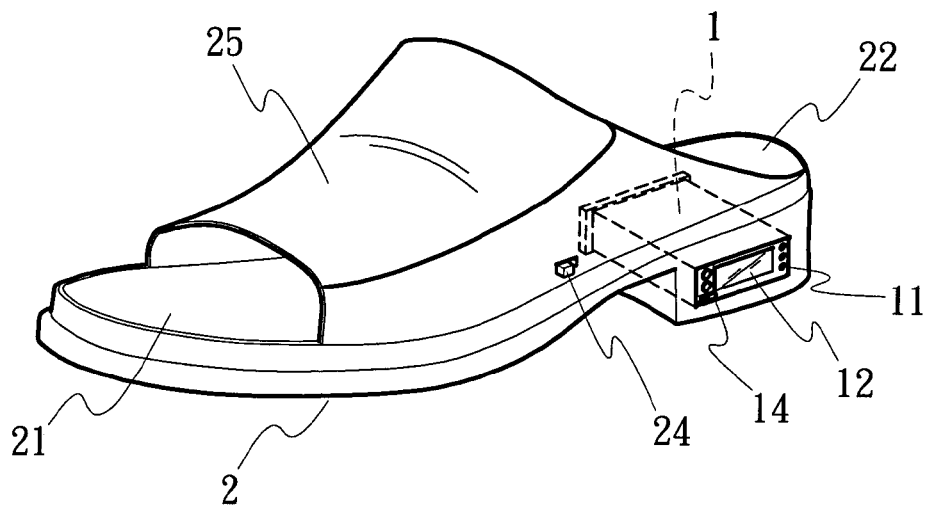
FIG. 4 shows the massage shoe in FIG. 3 wherein the controller is installed within the heel of the shoe body.
Figure 5:
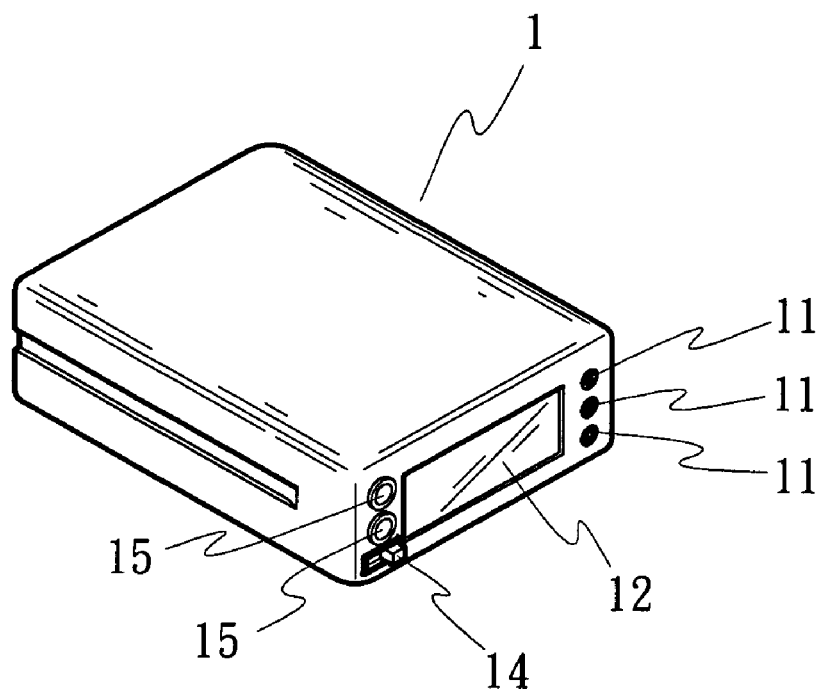
FIG. 5 is a perspective view of a controller of embedded type.
Figure 6:
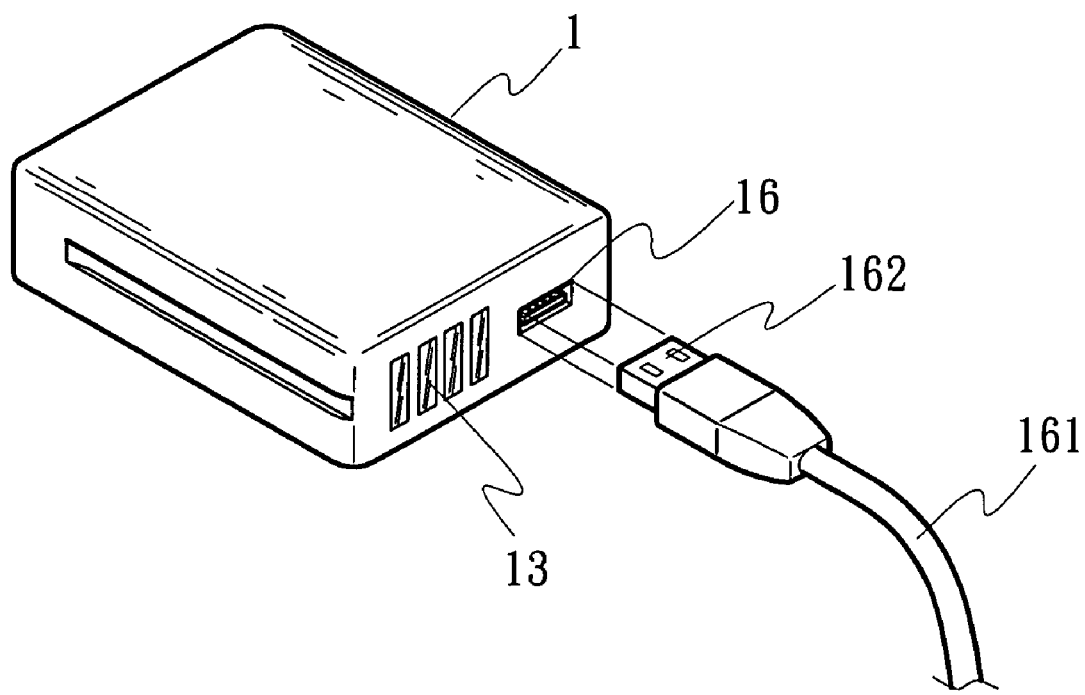
FIG. 6 is another perspective view of the controller in FIG. 5.

The above preferred embodiment has the controller 1 attached on a vamp 25 of a shoe body 2. In the next preferred embodiment, a controller 1 is embedded within the heel 26 of a shoe body 2, as shown in FIGS. 3 and 4. The heel 26 has a receptacle 261 for housing the controller 1. An inner wall of receptacle 261 is provided with a circuit board 262 and a set of conducting terminals 263, both of which are connected to conducting wires 211, 221. The controller 1 further includes a set of conducting terminals 13 corresponding to the conducting terminals 263, as shown in FIGS. 5 and 6. Thereby, the controller 1 can be inserted in to the receptacle 261 so that the conducting terminals 13 and the conducting terminals 263 will be engaged, and a mid-or-low-frequency electromagnetic wave massage can be provided.

Figure 7:
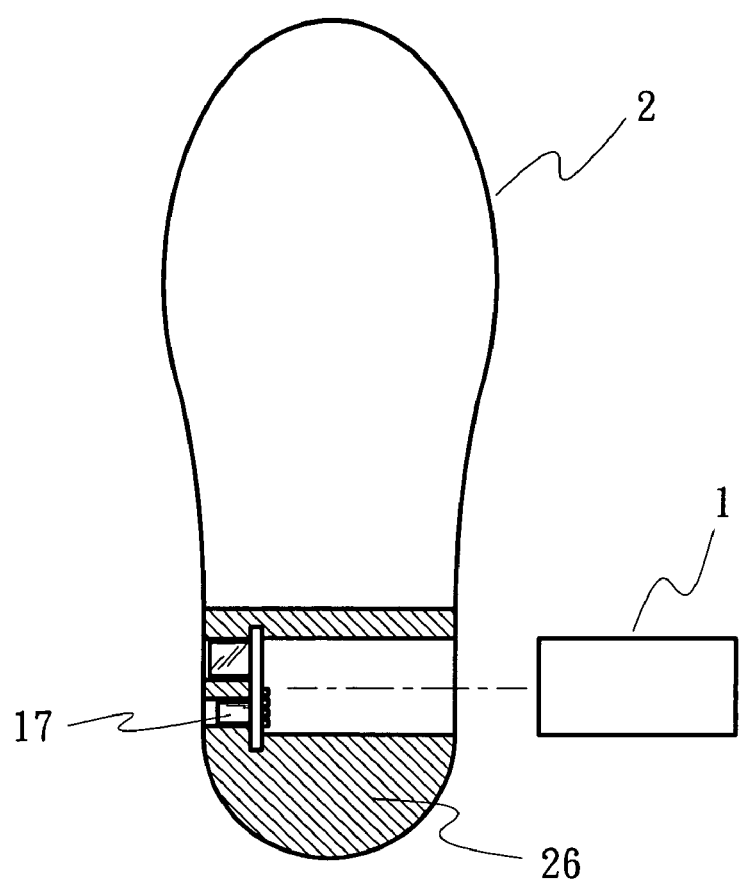
FIG. 7 is a bottom view of the massage shoe in FIG. 3 wherein the controller is installed within the heel of the shoe body.
Figure 8:
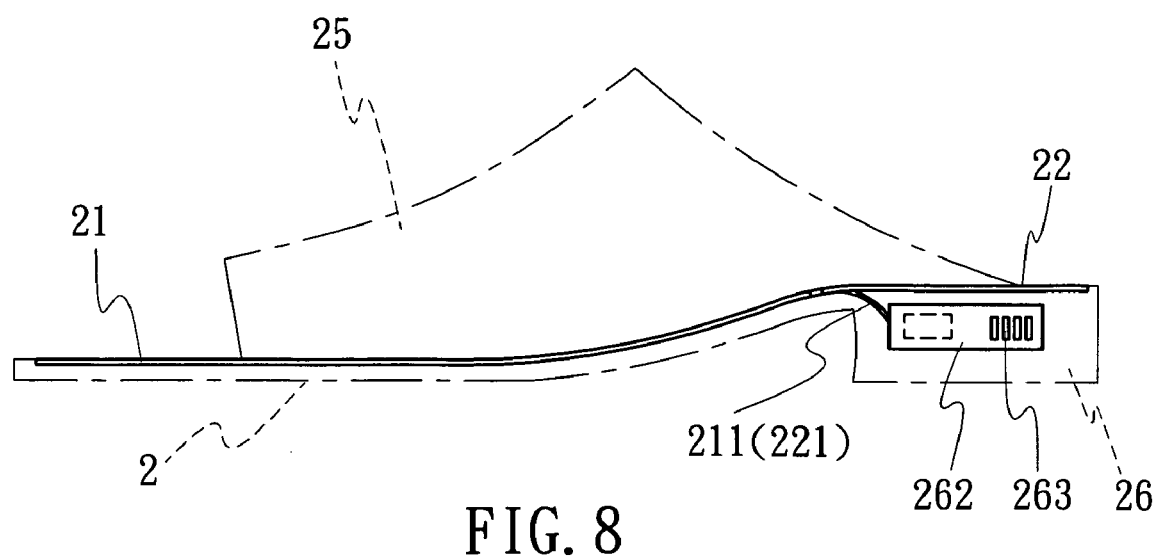
FIG. 8 is a lateral view of the massage shoe in FIG. 3 wherein the controller is installed within the heel of the shoe body.
Figure 9:
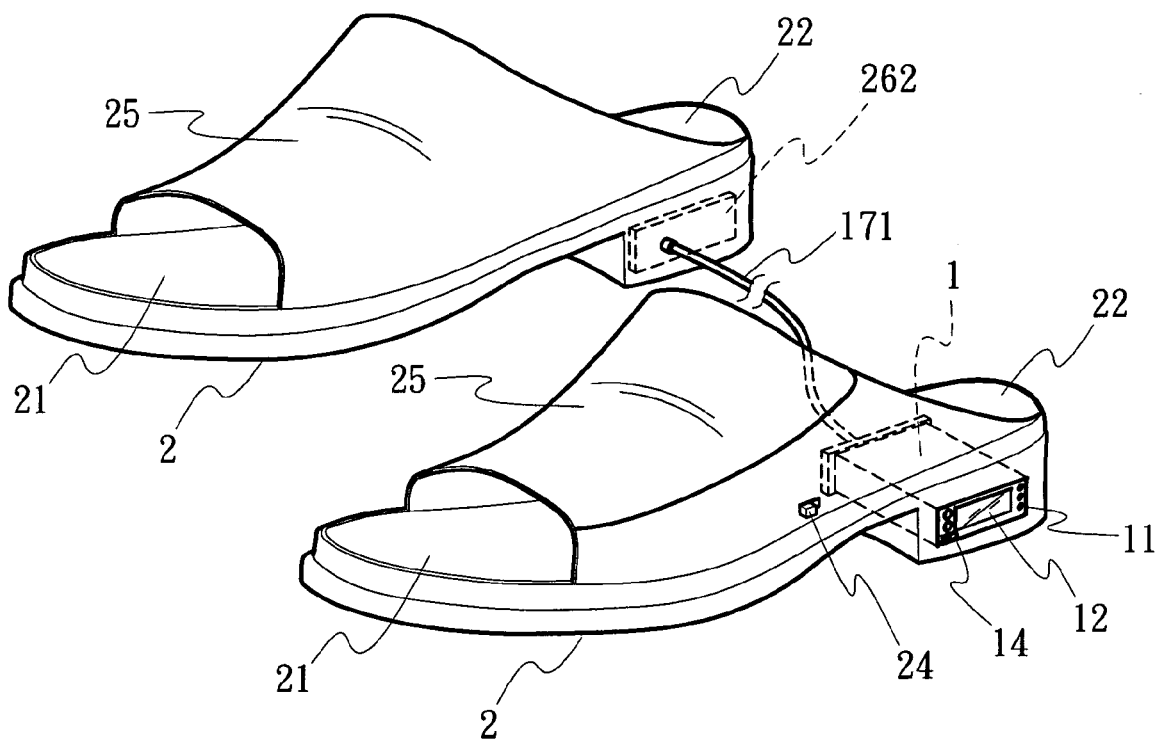
FIG. 9 is a perspective view of a pair of massage shoes connected by a wire.

The controller 1 of the above preferred embodiment, as shown in FIGS. 5 and 6, is provided with a plurality of control keys 11, an LCD display 12, and a set of conducting terminals 13 installed on the rear face of the controller 1. It further includes a power switch 14 for turning on/off the controller 1, at least two sockets 15 for connecting external devices, and a socket for an extended wire 16. The circuit board 262 and the conducting terminals 13 thereby form a connection port 17, as shown in FIGS. 7 and 8. The LCD display 12 is for displaying the operation mode. The conducting terminals 13 of the controller 1 can be connected to the conducting terminals 263 of the heel 26. The socket for an extended wire 16 matches a connecting head 162 of a extended wire 161, whereby the controller 1 can be removed from the shoe body 2, forming a remote wire control means. The connection port 17 is for connecting another extended wire 171, so that a pair of shoe bodies 2 may connected, as shown in FIG. 9.

Figure 10:
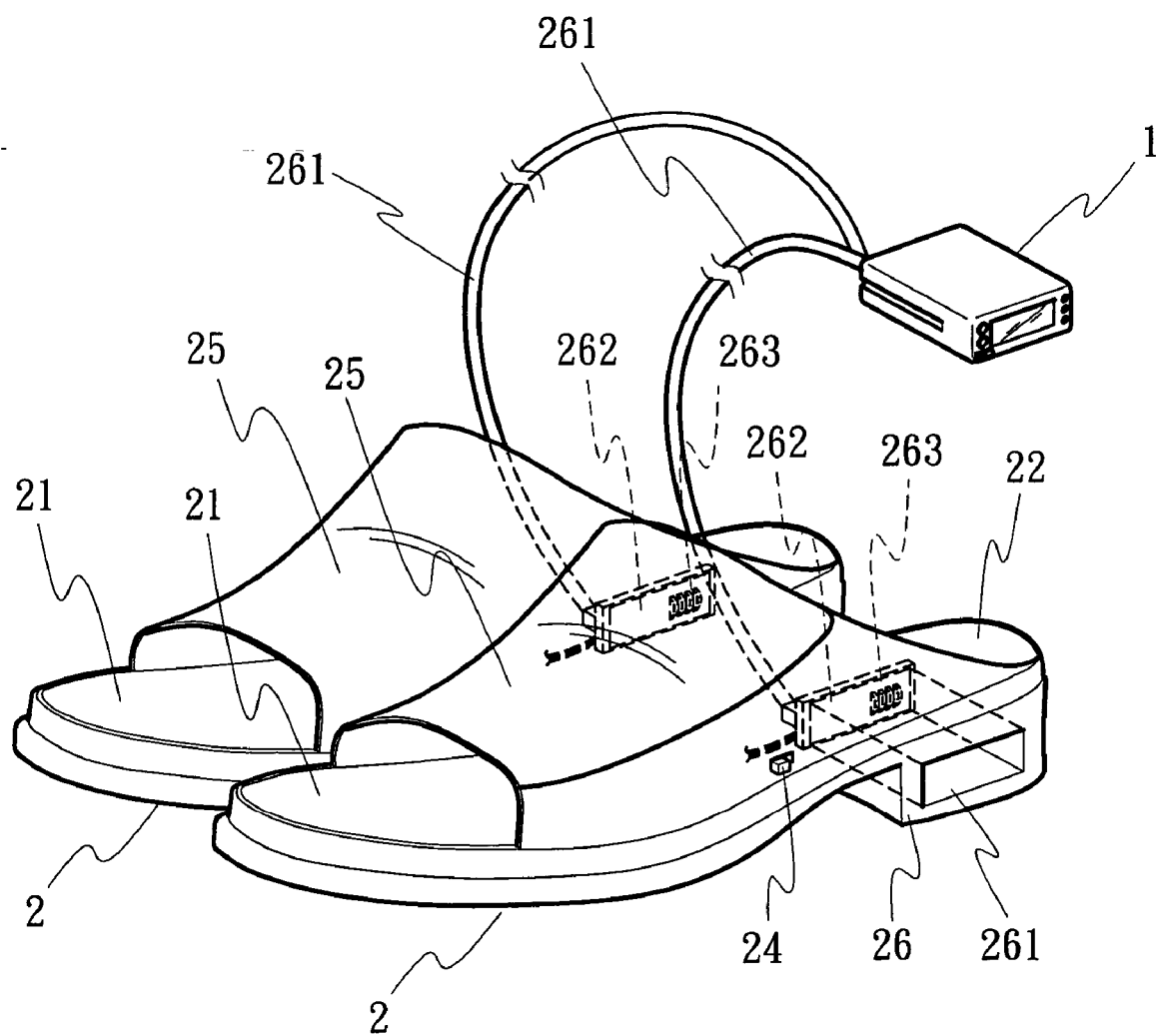
FIG. 10 is a perspective view of a pair of massage shoes sharing a controller.

Referring FIG. 10, a controller 1 can be further provided with two sockets for an extended wire 16 for connecting two extended wires 161, so that the controller 1 can be taken out of the receptacle 261 of a heel 26, which controller 1 controls both shoe bodies 2 simultaneously.

Figure 11:
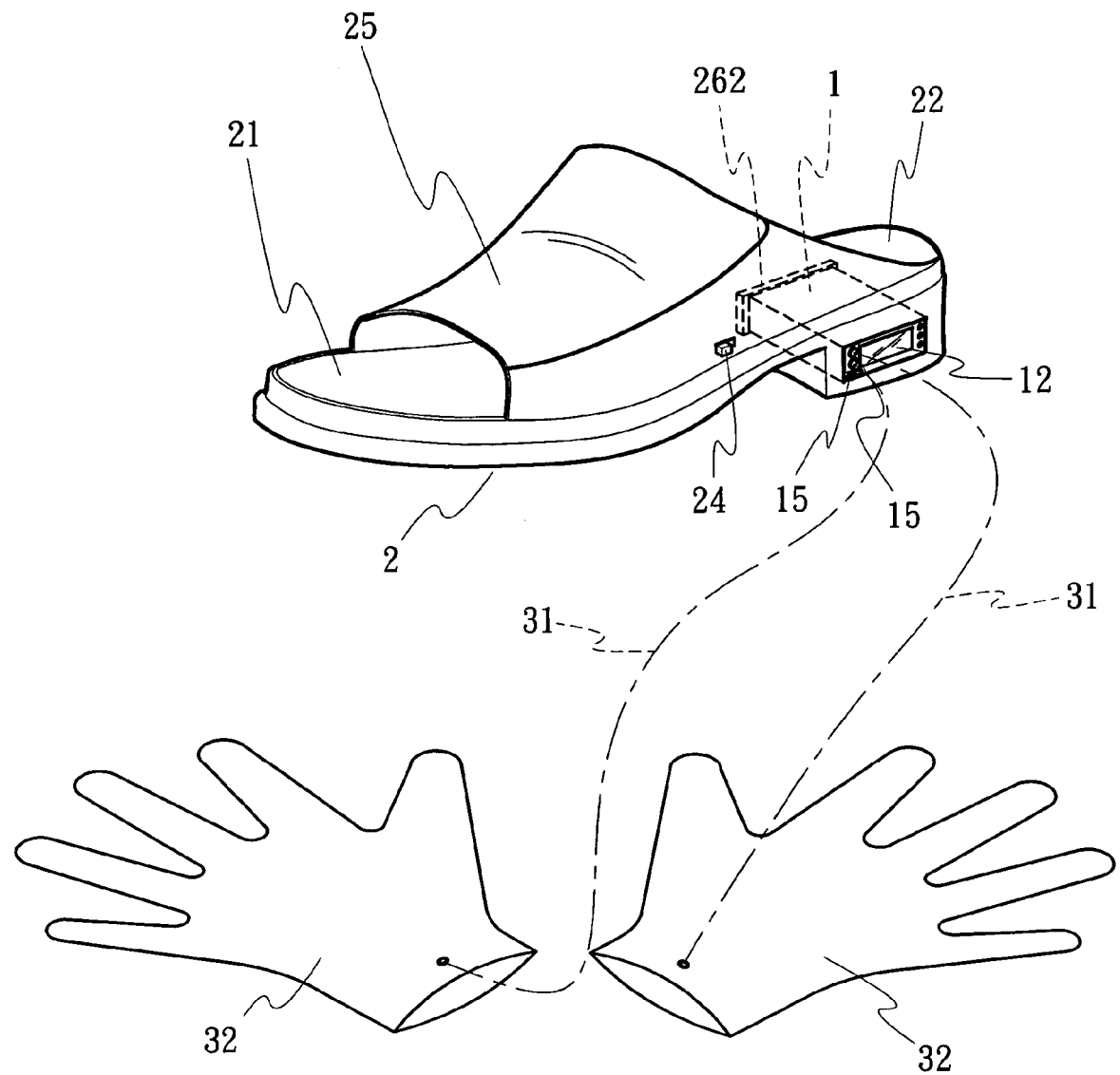
FIG. 11 is a perspective view of a massage shoe connected to a pair of conducting gloves.
Figure 12:
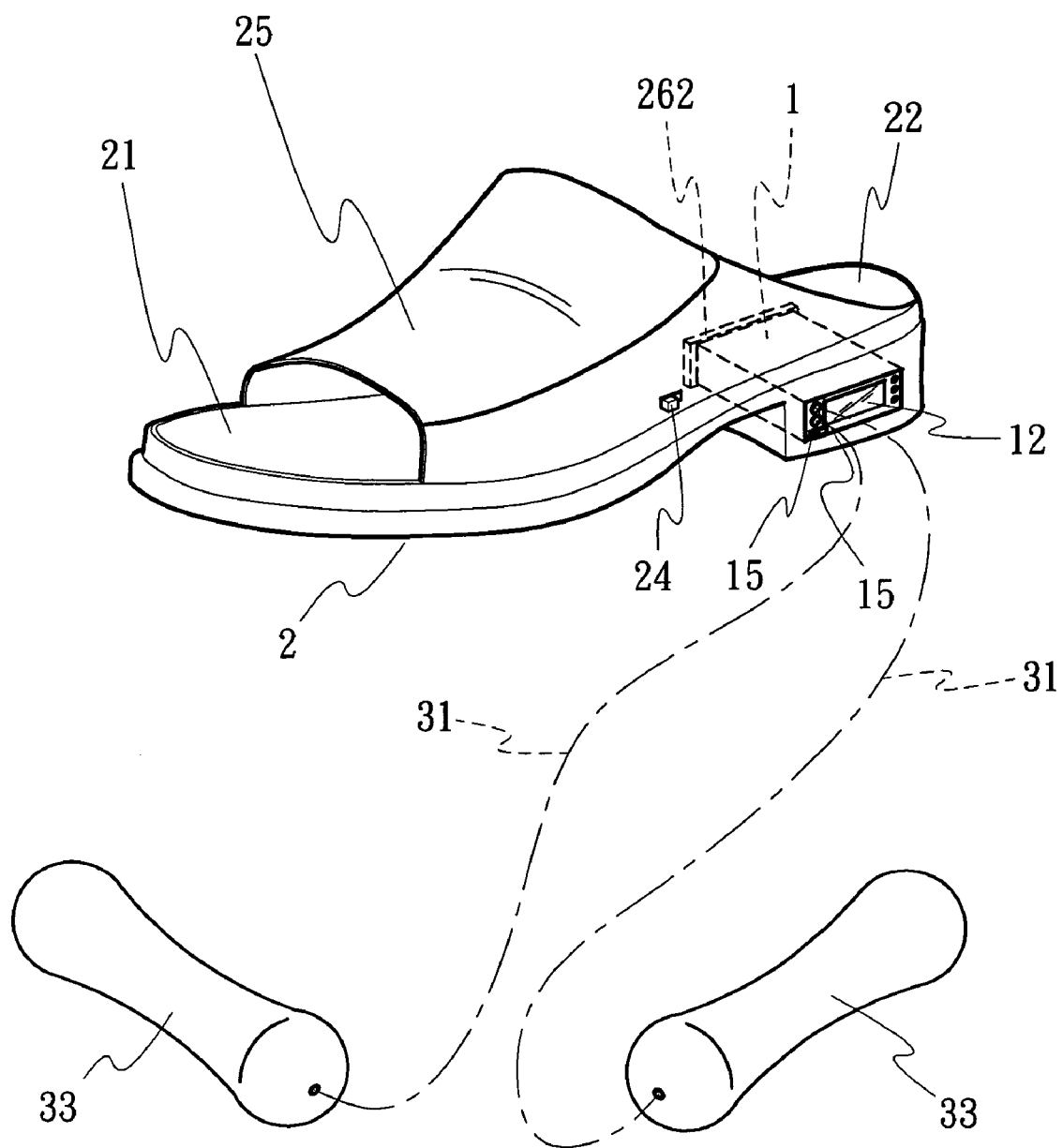
FIG. 12 is a perspective view of a massage shoe connected to a pair of conducting sticks.

Referring FIGS. 11 and 12, two sockets 15 for connecting external devices of the controller 1 can respectively connect a pair of conducting gloves 32 (as shown in FIG. 11) or a pair of conducting massage sticks 33 (as shown in FIG. 12) through a connection wire 31, whereby a user can wear the gloves or hold the sticks to acquire a mid-or-low-frequency electromagnetic wave massage.

Figure 13:
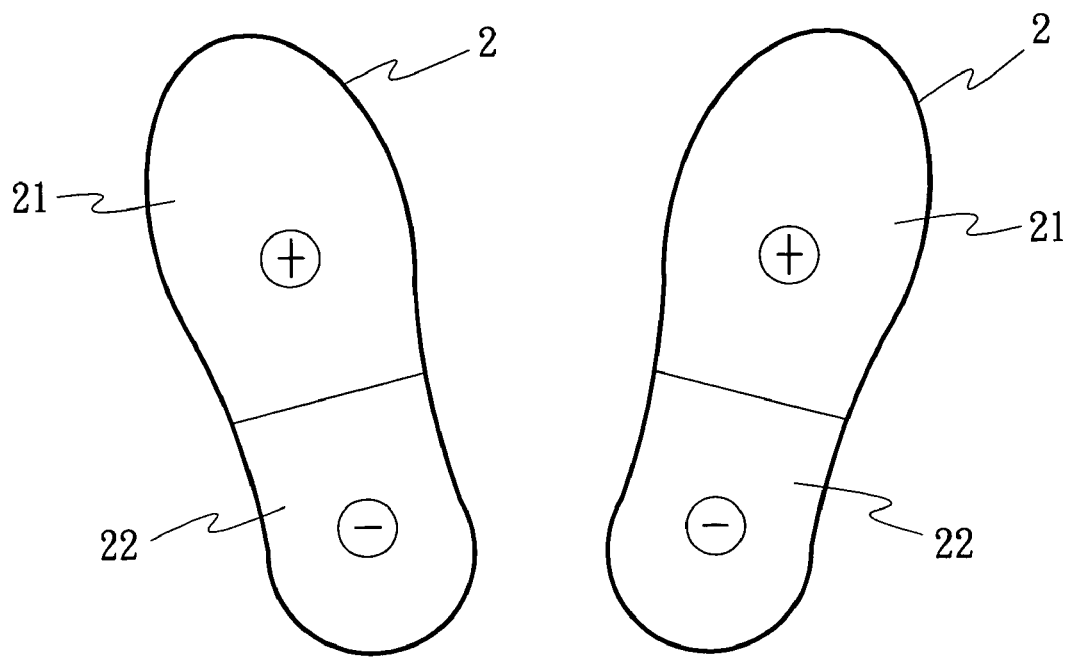
FIG. 13 shows a pair of massage shoes each having two electric polarities.
Figure 14:
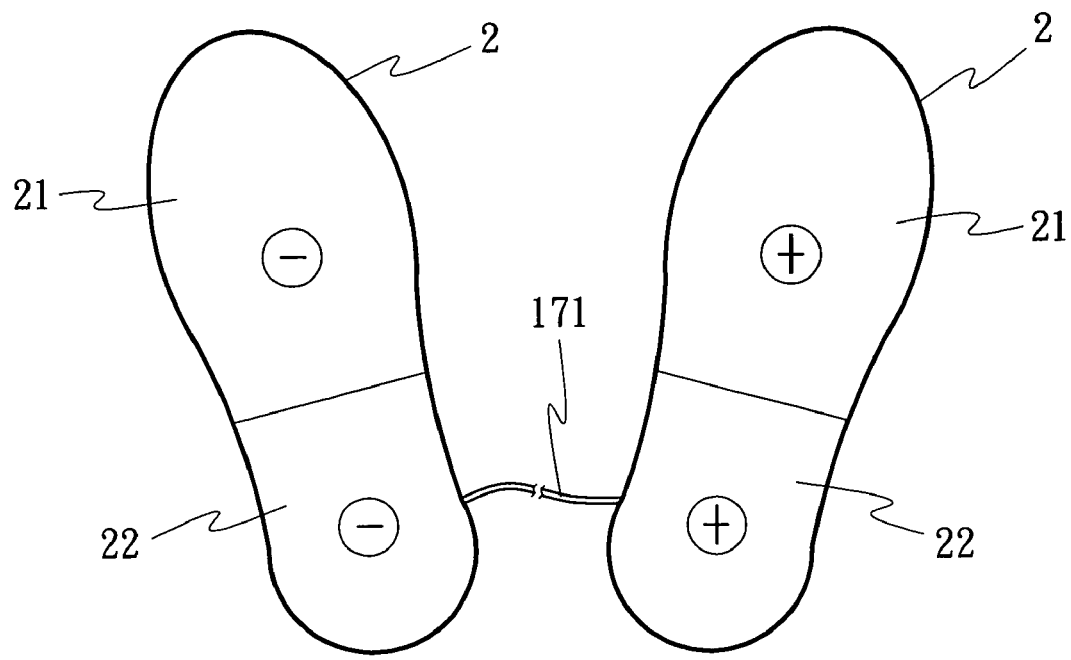
FIG. 14 shows a pair of massage shoes with opposite electric polarities.

Referring FIG. 13, the foot supporting surface (an insole) of the shoe body 2 of the present invention comprises two conducting sheets 21, 22, which by default have different electric polarities. However, the polarity of either of conducting sheets 21, 22 can be varied by the polarity switch 24, whereby the massage effect can applied to a foot or both feet, if two shoe bodies 2 are connected. That is, each of the shoe body 2 can be of single polarity or two opposite polarities. When two shoe bodies 2 are each of single polarity, the shoe bodies 2 have opposite polarities; thereby, a global mid-or-low-frequency electromagnetic wave massage across two feet can be provided.

Figure 15:
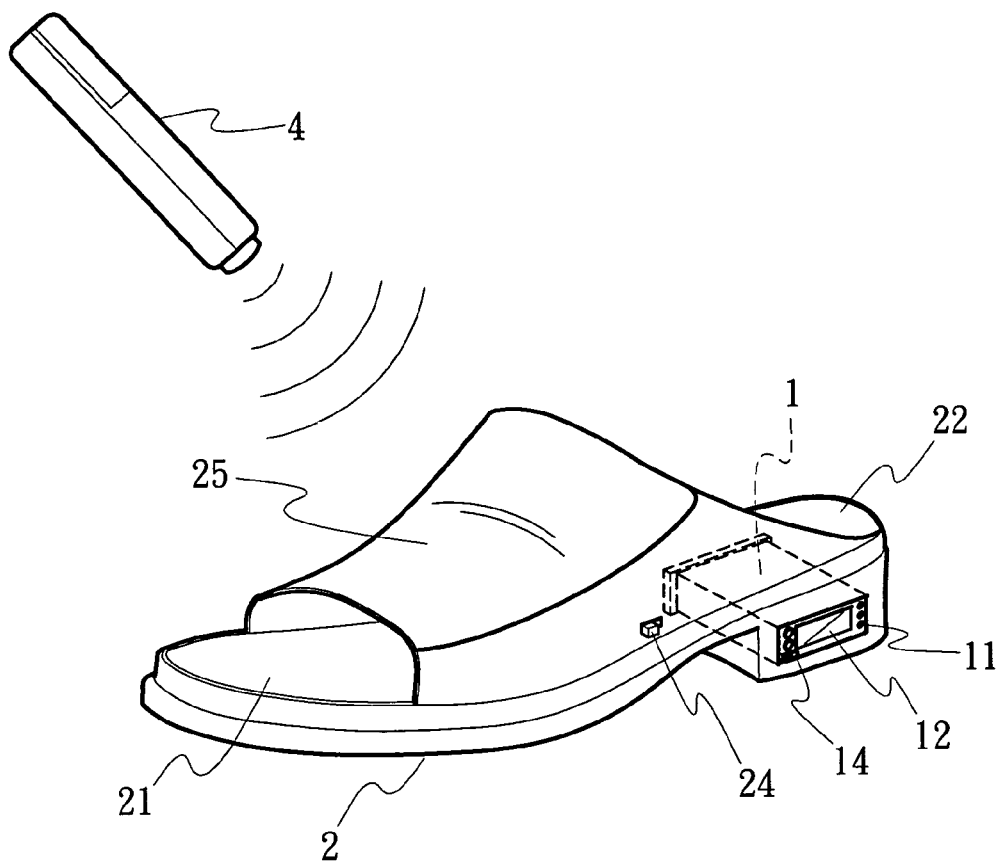
FIG. 15 is a perspective view of a massage shoe controlled by a wireless controller.
Figure 16:
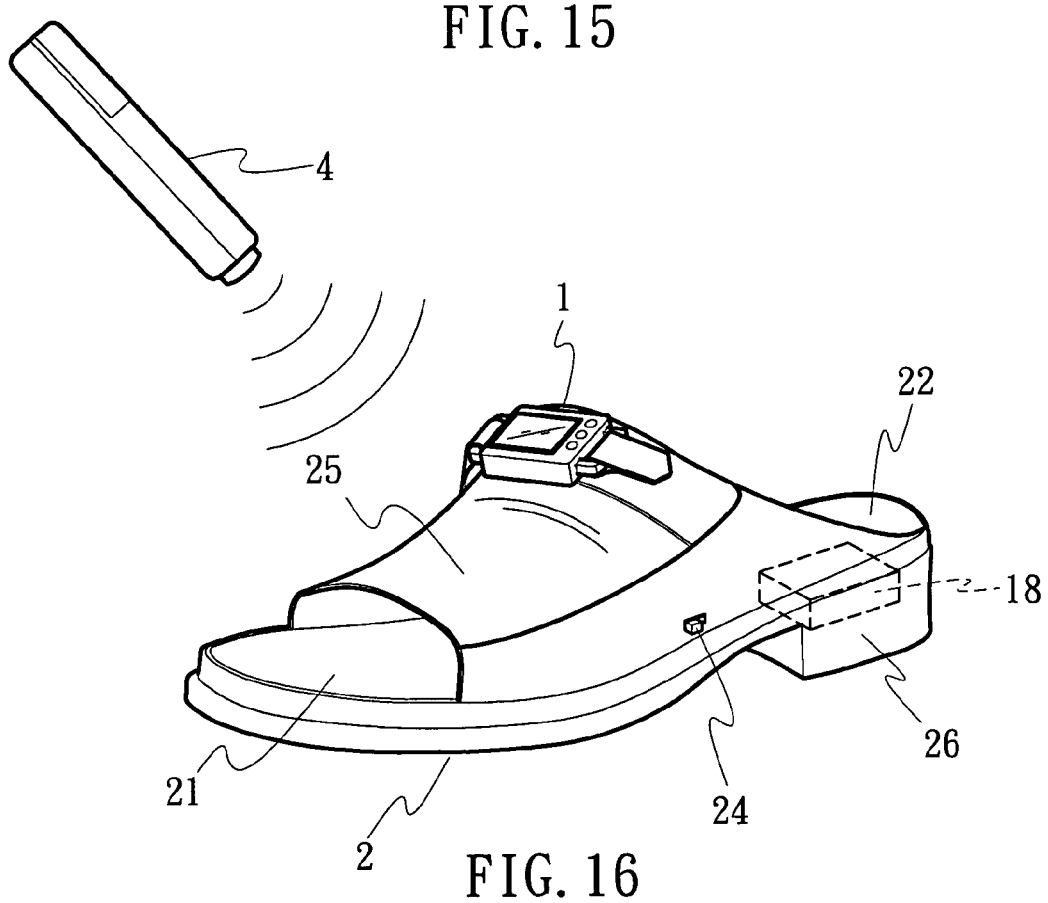
FIG. 16 is a perspective view of another massage shoe controlled by a wireless controller.

In addition to the attachment on a vamp 25 or within a heel 26 of a shoe body 2, the controller 1 can be a separate entity connected to the shoe body 2 with a wire. Alternatively, a wireless control means can be provided, as shown in FIGS. 15 and 16. In the wireless control, a transmitter and a receiver are respectively added to a remote control device 4 and the controller 1.

Figure 17:
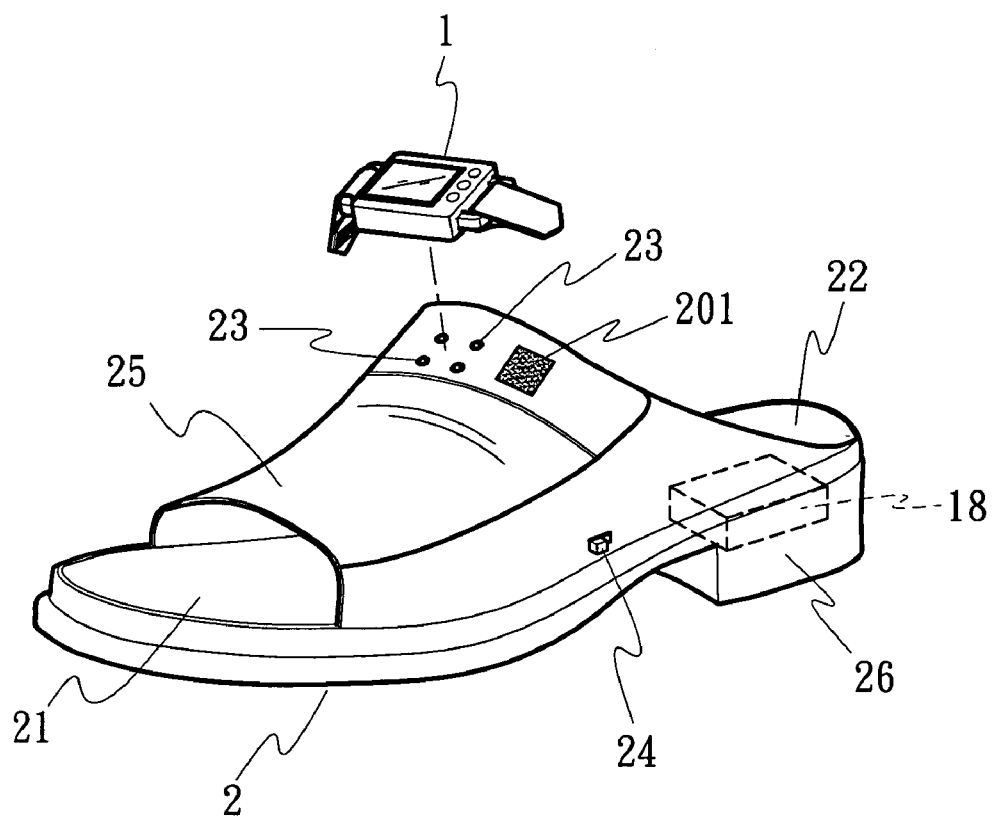
FIG. 17 is a perspective view of a massage shoe wherein the battery room and the controller are separate.
Figure 18:
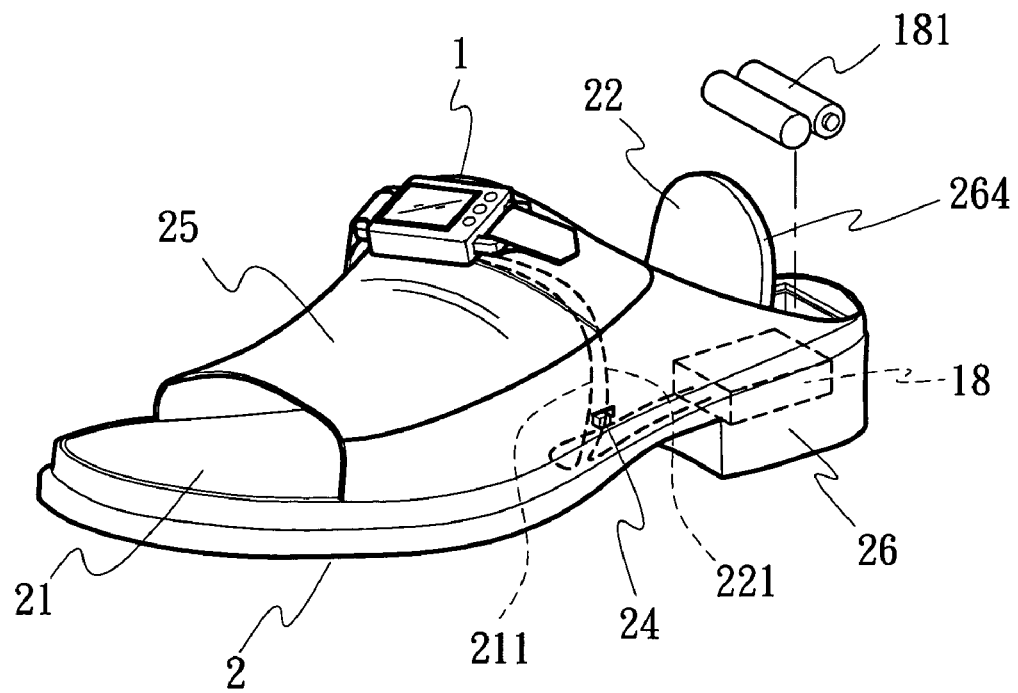
FIG. 18 is a perspective view of the massage shoe in FIG. 17 wherein the batteries are taken from the battery room.
Figure 19:
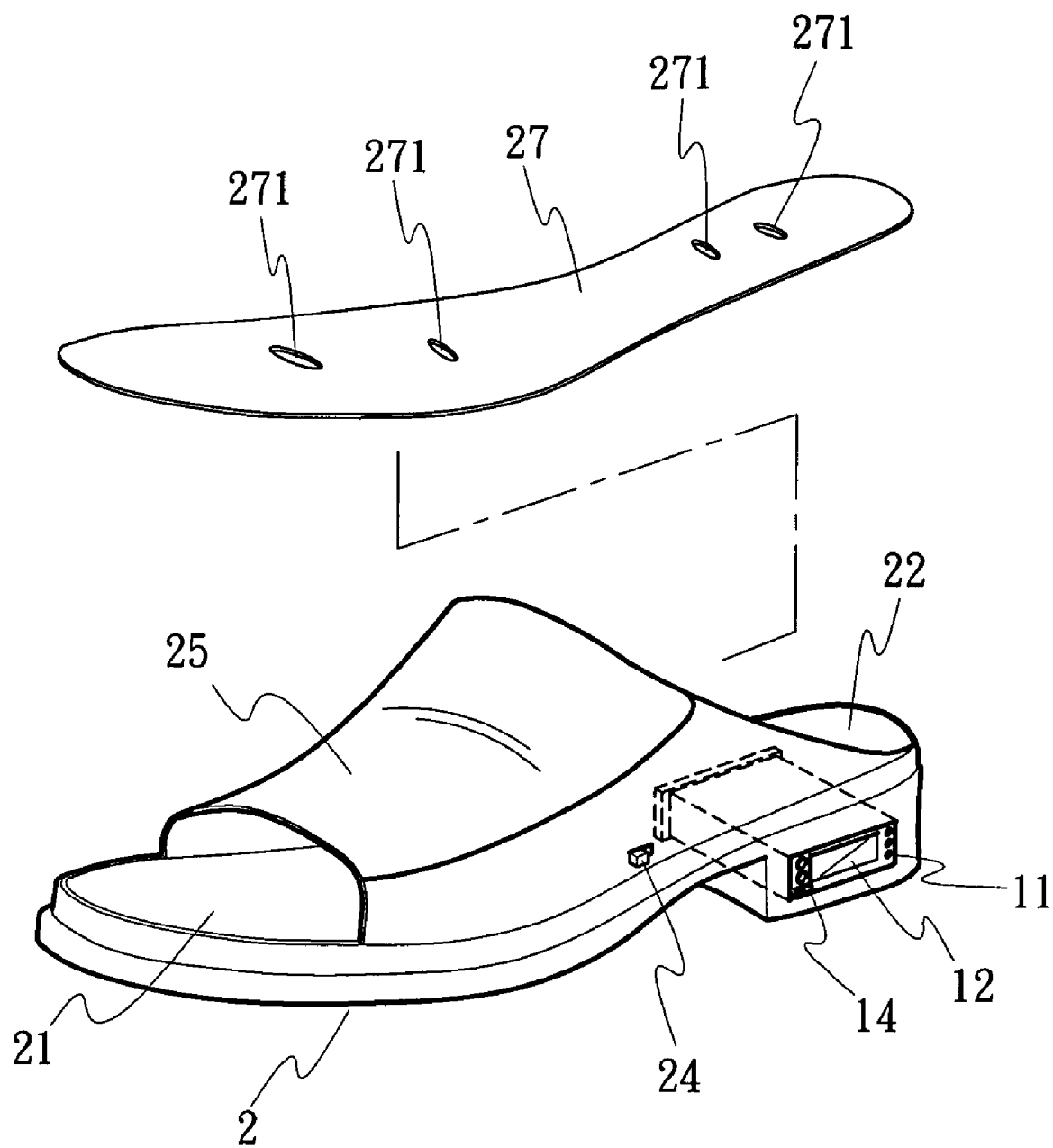
FIG. 19 shows a massage shoe of the present invention used with an insulating shoe pad.

The batteries 181 for the controller 1 can be housed in a battery room in the controller 1, as shown in FIG. 17, or they can be housed in a separate battery mount 18, whereby the batteries 181 can be hidden in a heel 26. The heel 26 further includes a cover 264 shielding the opening of the battery mount 18, facilitating the replacement of batteries 181.

The controller 1 to be embedded within a shoe body 2 may be further provided with retaining grooves 19, and the inner walls of the receptacle 261 within the heel 26 may be further provided with retaining members. Thereby, the controller 1 can situate stably in the receptacle 261 as long as the retaining grooves 19 and the retaining members are engaged.

Referring to 19, the conducting sheets 21, 22 of the shoe body 2 is further covered by an insulating shoe pad 27 having a plurality of conducting holes 271 at selected locations, corresponding to some acupuncture points of a foot. The insulating shoe pad 27 is a thin insulating sheet, and the conducting holes 271 are through holes. Alternatively, the conducting holes 271 are filled with a conducting material. Thereby, only locations on a foot in contact with those conducting holes will experience an electromagnetic wave massage.

Figure 20:
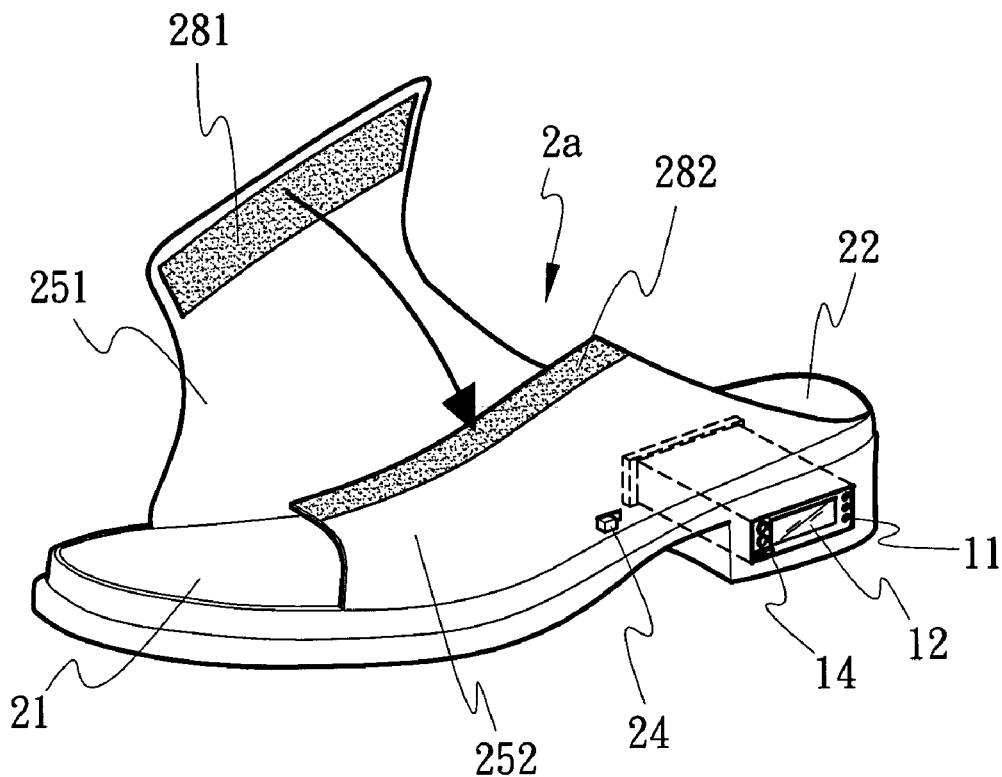
FIG. 20 is a perspective view of a massage shoe of the present invention wherein the vamp is formed by two opposite vamp pieces.

The style of the shoe body 2 of the present invention may vary arbitrarily without restriction to the styles of the above preferred embodiments. For example, the shoe body 2a disclosed in FIG. 20 has two opposite vamps 251, 252 capable of being combined by a pair of adhesive straps 281, 282, whereby the tightness of vamp can be adjusted.

Figure 21:
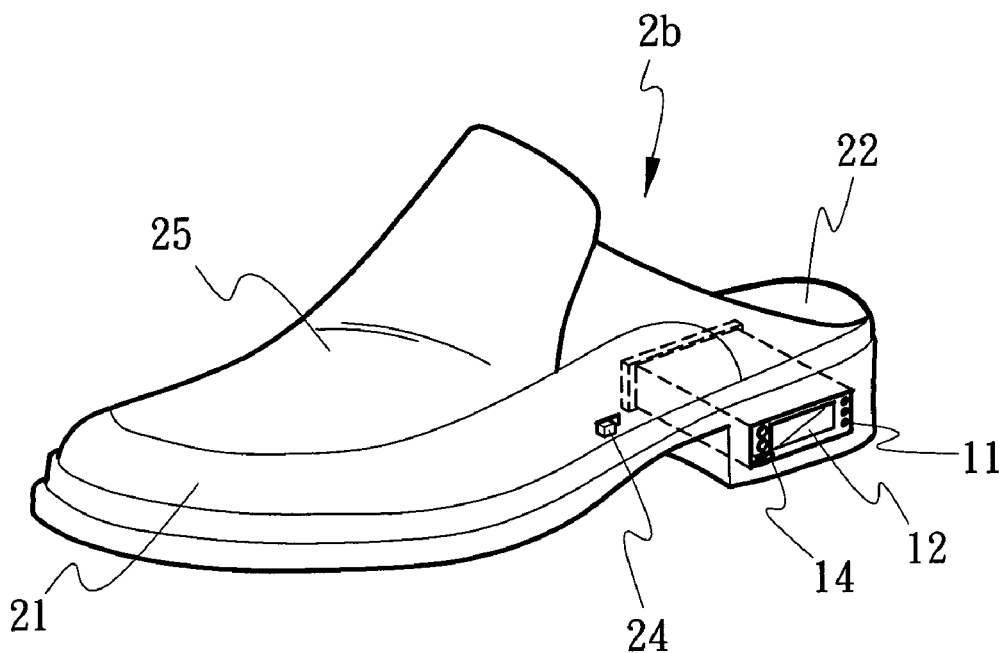
FIG. 21 is a perspective view of a massage shoe of the present invention differing in style.

Referring to FIG. 21, a shoe body 2b of another style is disclosed. Therefore, the present invention can be applied to different shoes, such as slippers, sandals, sneakers, leather shoes, mountaineering boots and informal shoes. The massage shoes of either type can be used as ordinary footwear. By connecting a controller 1, an effect of mid-or-low-frequency electromagnetic wave massage is provided.

Figure 22:
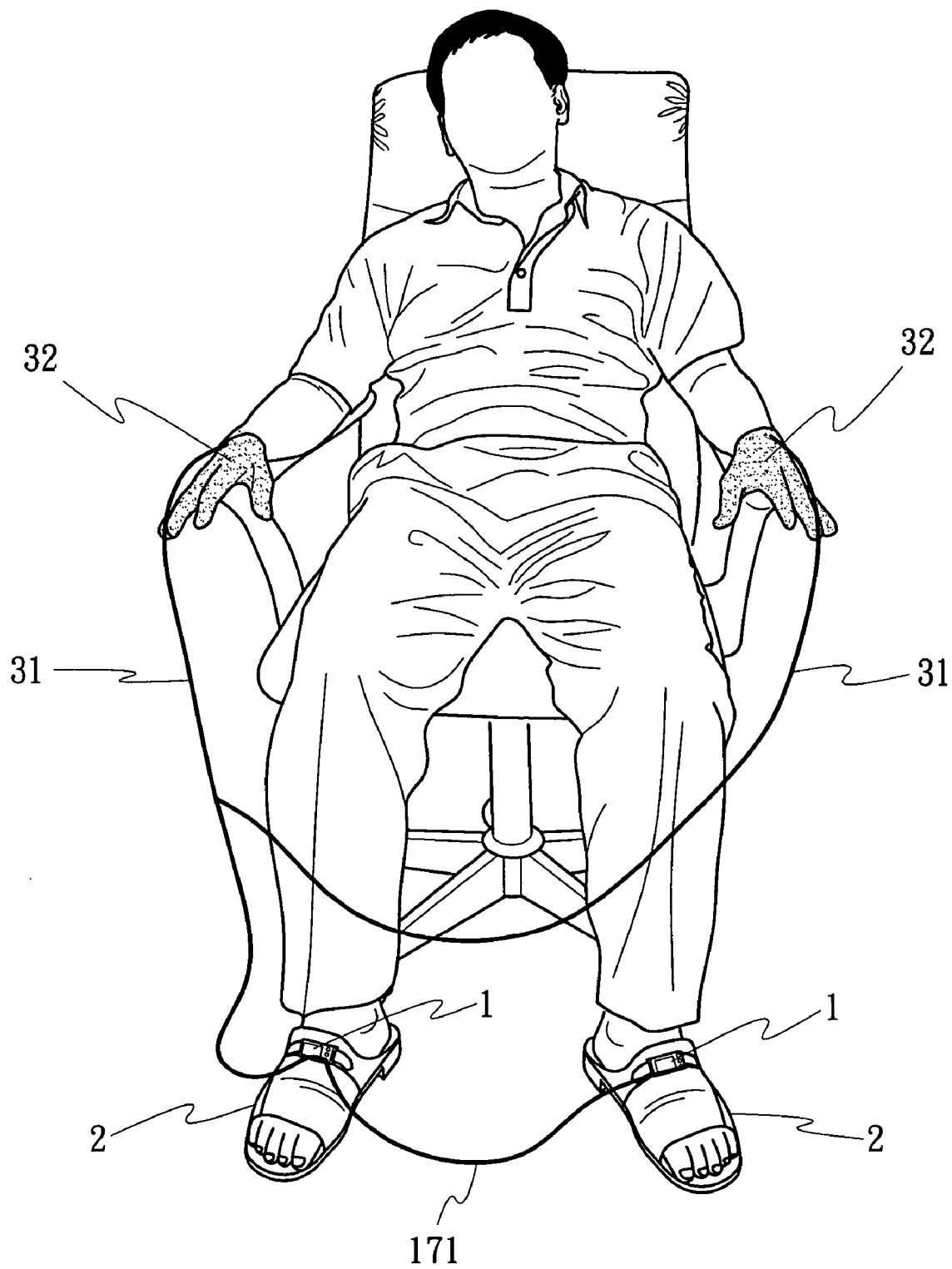
FIG. 22 shows the present invention used together with a pair of conducting gloves.

Referring to FIG. 22, the present invention used with a pair of conducting massage gloves 32 can extend the massage effect to the whole body.

The present invention is thus described, and it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A pair of massage shoes, each comprising:
   a shoe body having a plurality of conducting sheets installed on a foot supporting surface therein, a heel of said shoe body being provided with a receptacle, said receptacle having a circuit board and a plurality conducting terminals for connecting said conducting sheets through conducting wires; and
   a controller having a plurality of conducting terminals for engaging said conducting terminals of said shoe body after said controller is inserted into said receptacle, said controller transmitting high-voltage electric pulses to said shoe body through said engaged conducting terminals, whereby a massage effect by electromagnetic waves will be applied to the bottom surfaces of two feet.

2. The pair of massage shoes of claim 1, wherein said controller has a central integrated circuit for generating and transmitting electric pulses, whereby the inductors and capacitors therein will be discharged to generate high-voltage signals whose bandwidth can be modified by preset programs.

3. The pair of massage shoes of claim 1 wherein said controller further includes a plurality of control keys, an LCD display, a set of conducting terminals installed on a rear face of said controller for forming a connection port after connecting said circuit board through said conducting terminals of said shoe body, a power switch, at least two sockets for connecting external devices, and at least a socket for an extended wire, whereby said controller can be connected to an extended wire to form a wired remote control means.

4. The pair of massage shoes of claim 1 further comprising a polarity switch for changing the polarity of each of said conducting sheets.

5. The pair of massage shoes of claim 1 wherein a heel of said shoe body is provided with a receptacle for housing said controller.

6. The pair of massage shoes of claim 1 wherein said controller is capable of powering an electric massage device selected from a pair of conducting massage gloves and a pair of electric massage sticks through a pair of connection wires.

7. The pair of massage shoes of claim 1 wherein said controller is controlled by a remote wireless device.

8. The pair of massage shoes of claim 1 wherein said controller is further provided with a plurality of retaining grooves, and wherein inner walls of said receptacle is further provided with a plurality of retaining members, whereby said controller will be embedded in said the receptacle upon the engagement between said retaining grooves and said retaining members.

9. The pair of massage shoes of claim 1 wherein said conducting sheets of said shoe body is further covered by an insulating shoe pad having a plurality of holes at selected locations, corresponding to some acupuncture points of a foot.

10. The pair of massage shoes of claim 9 wherein said insulating shoe pad is a thin insulating sheet, and said holes are through holes.

11. The pair of massage shoes of claim 9 wherein said insulating shoe pad is a thin insulating sheet, and said holes are filled with a conducting material.

12. A pair of massage shoes, each comprising:
   a shoe body having a plurality of conducting sheets installed on a foot supporting surface therein, said conducting sheets being respectively connected by conducting wires to a selected location in said shoe body, a plurality of conducting snap sockets forming at said selected location; and
   a controller capable of being attached onto said shoe body by securing with said conducting snap sockets, said controller having an internal circuitry forming an output terminal having a plurality of condutive terminals for transmitting high-voltage electric pulses to said shoe body through said conducting snap sockets, whereby a massage effect by electromagnetic waves will be applied to the bottom surfaces of two feet.

13. The pair of massage shoes of claim 12 wherein said controller is attached on a vamp of said shoe body.

14. The pair of massage shoes of claim 12 wherein said battery mount is separated from said controller and inserted within a heel of said shoe body, said heel further including a cover for shielding said battery mount.

15. The pair of massage shoes of claim 12 wherein the shoe body has a polarity switch for controlling the polarities of the conducting sheets.

16. The pair of massage shoes of claim 12 wherein the controller has at least two sockets for being connected to other peripheral conductive device.

* * * * *